(12) United States Patent
Jäggi et al.

(10) Patent No.: US 6,997,930 B1
(45) Date of Patent: Feb. 14, 2006

(54) DEVICE FOR INJECTING BONE CEMENT

(76) Inventors: Kurt Jäggi, Kastanienweg 53, 3095 Spiegel b. Bern (CH); Paul Heini, Eichholzstrasse 103 C, 3084 Wabern (CH)

( * ) Notice: Subject to any disclaimer, the term of this patent is extended or adjusted under 35 U.S.C. 154(b) by 443 days.

(21) Appl. No.: 10/311,978

(22) PCT Filed: Jun. 30, 2000

(86) PCT No.: PCT/CH00/00355

§ 371 (c)(1),
(2), (4) Date: Dec. 23, 2002

(87) PCT Pub. No.: WO02/02033

PCT Pub. Date: Jan. 10, 2002

(51) Int. Cl.
*A61F 2/46* (2006.01)

(52) U.S. Cl. ...................................................... 606/93

(58) Field of Classification Search ............ 606/92–94; 604/93.01, 158, 161, 164.01, 164.02, 164.06, 604/164.07, 164.13, 264, 167.01–167.05
See application file for complete search history.

(56) References Cited

U.S. PATENT DOCUMENTS

| 4,595,006 A | | 6/1986 | Burke |
| 4,969,888 A | | 11/1990 | Scholten |
| 5,080,655 A | * | 1/1992 | Haaga ........................ 604/265 |
| 5,360,416 A | * | 11/1994 | Ausherman et al. ........ 604/272 |
| 5,487,392 A | | 1/1996 | Haaga |
| 5,775,333 A | | 7/1998 | Burbank |

FOREIGN PATENT DOCUMENTS

WO        9949819        10/1999

* cited by examiner

*Primary Examiner*—Eduardo C. Robert
*Assistant Examiner*—D. Jacob Davis
(74) *Attorney, Agent, or Firm*—Morgan, Lewis & Bockius LLP

(57) ABSTRACT

In a device for injecting bone cement, the discharge direction of the bone cement after insertion of the cannula should be controllable in a certain region. This is made possible through a radial exit aperture which is provided on the front end of the cannula. Since the cannula is inserted with the aid of a guide wire, it has an orifice on its front end, which orifice must be closed off by means of a ball prior to the injection. A plunger serves to insert the ball. So that the situation of the radial aperture is known at all times, even with inserted cannula, the handle of the cannula has an asymmetrical shape.

11 Claims, 3 Drawing Sheets

FIG. 3a
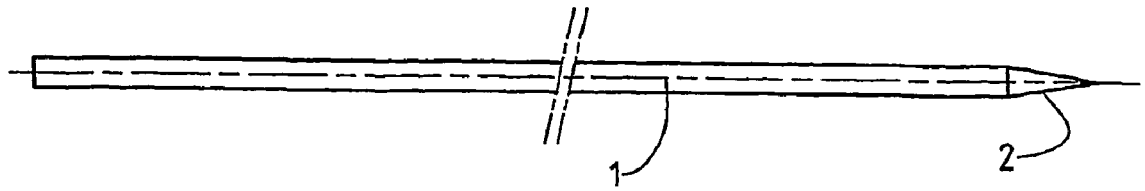
FIG. 3b
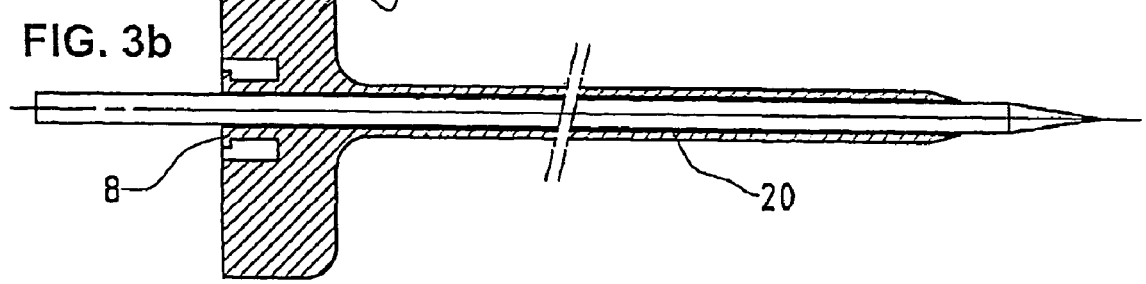
FIG. 3c
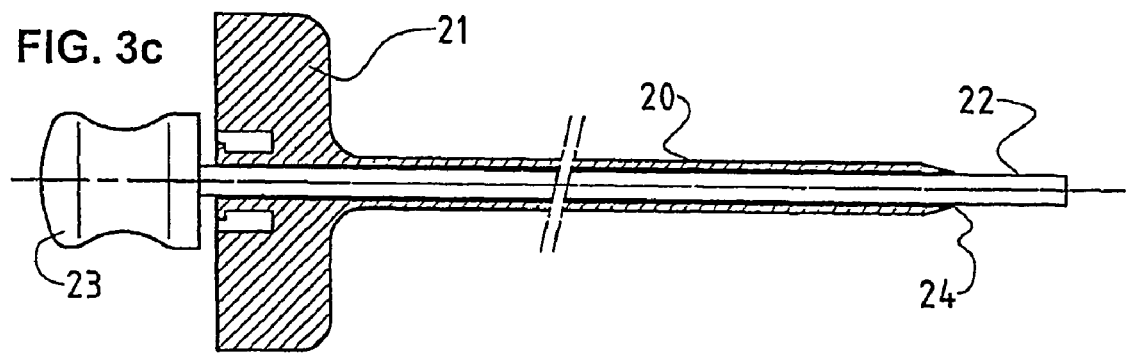
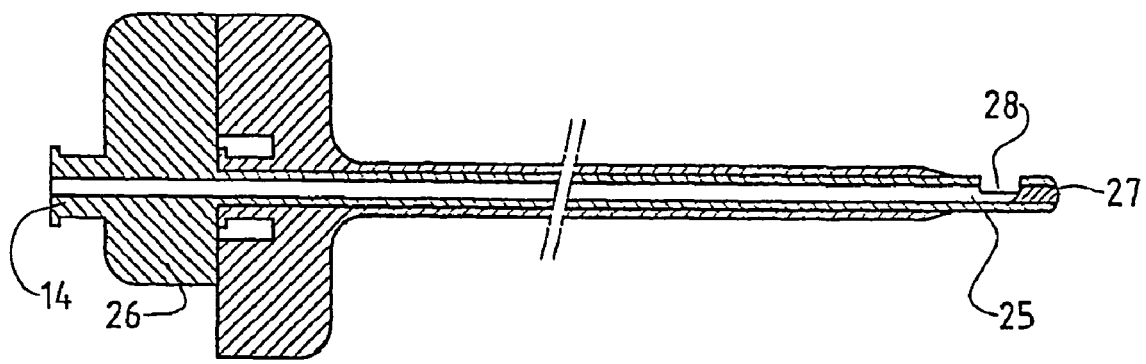
FIG. 3d

DEVICE FOR INJECTING BONE CEMENT

BACKGROUND

The invention relates to a device for injecting bone cement, containing a guide wire and a cannula fitting snugly on the guide wire at least with the inner diameter of its front axial orifice.

Augmenting osteoporotic bones with injected bone cement for fracture prophylaxis is already known. With the injection cannulae used so far with axial exit aperture, the filling cannot be placed with the desired precision in many cases.

SUMMARY OF THE INVENTION

It is therefore an object of the invention to propose a device for injecting bone cement in which the discharge direction of the bone cement after insertion of the cannula is able to be guided into a particular area.

According to a first variant of the invention, this object is achieved in that there are closing off means with which the front, axial orifice of the cannula is closable after removal of the guide wire and in that the cannula has a radial aperture, for exit of the bone cement, near the front, axial orifice.

According to a special embodiment of this variant, the closing off means is an inner cannula, closed on its front end, which inner cannula is insertable in the cannula in such a way that its front end closes the orifice of the cannula tightly and has a radial aperture near its front, closed end.

According to another, especially preferred embodiment of the first variant, the diameter of the front, axial orifice of the cannula is smaller than the inner diameter of the cannula and the closing off means is a stopper, the largest diameter of which is larger than the diameter of the front, axial orifice of the cannula. When the orifice is closed off by the stopper, the entire inner cross-section of the cannula is available for the passage of the bone cement so that in this embodiment the flow resistance for the bone cement is considerably less than with the previously mentioned embodiment.

According to a second variant of the invention, this object is achieved in that an inner cannula is provided, closed at its front end, which has near the front, closed end a radial aperture for exit of the bone cement and which fits snugly in the front axial orifice of the cannula at least in a region close to the edge, remote from its front end, of the radial aperture, whereby, after removal of the guide wire, the inner cannula is insertable so far into the cannula that its radial aperture extends beyond the cannula.

Special embodiments of the invention will be explained in the following, by way of example, with reference to the attached drawings.

BRIEF DESCRIPTION OF THE DRAWINGS

FIGS. 3a to 3d show a third embodiment example of a device according to the invention in which the cannula is surpassed in the front by an inner cannula with radial aperture.

FIGS. 1a, 2a and 3a each show a guide wire 1 which is pointed at its front end 2. This front end 2 of the guide wire is driven forward, under X ray control, into the bone up to some millimeters beyond the place at which the bone cement is supposed to be injected. The guide wire typically has a diameter of 2.5 mm and a length of 180 mm; the invention should not be limited, however, to these dimensions.

DETAILED DESCRIPTION OF THE INVENTION

Figure 1A:
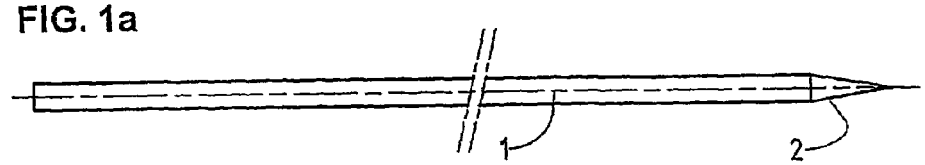
FIGS. 1a to 1d show a first embodiment example of a device according to the invention with a cannula with radial aperture and an inner cannula, which likewise has a radial aperture.
Figure 1B:
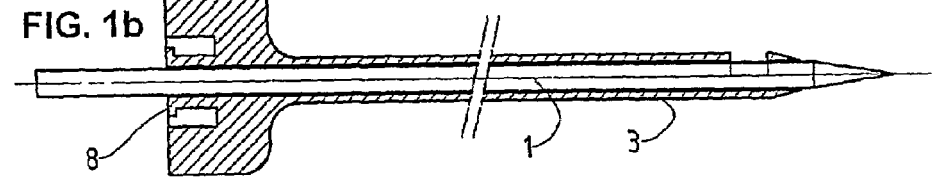

According to the embodiment example according to FIGS. 1a to 1d, a cannula 3 is pushed over the guide wire. This cannula 3 has at its front end an orifice 4 with a sharply ground circumferential edge whose inner diameter fits snugly over the guide wire. By means of this design, bone tissue is prevented from getting into the interior of the cannula 3 during forwards pushing of the cannula 3. Disposed on the rear (in the drawing left) end of the cannula is a handle 6. The orifice 4 of the cannula can be slightly reduced and the remaining inner diameter of the cannula can be 3.1 mm, for example. The outer diameter of the cannula 3 can be 4 mm, for instance, and its length up to the handle 130 mm. Disposed in the cannula near the orifice 4 is a radial aperture 5, the width of which is somewhat smaller than the inner diameter of the cannula. The length of this radial aperture 5 is at least the same as that of the aperture of the inner cannula 9 described further below. The handle is of asymmetrical shape, for instance with a pointer-like form the tip of which is aligned with the radial aperture 5, so that the surgeon knows the angular position of the radial opening 5 at all times. The handle 6 has moreover a recess 7 and a coupling 8, the function of which will be explained further below.

Figure 1C:
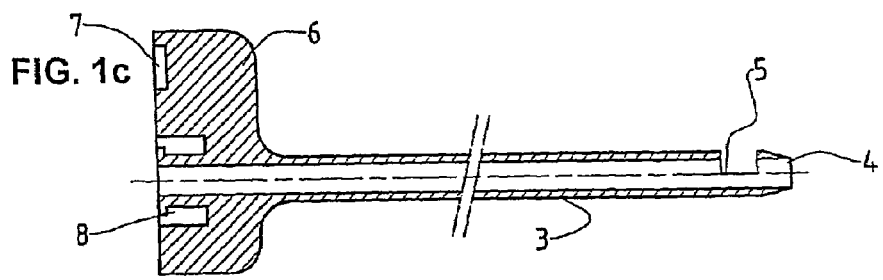

FIG. 1c shows the cannula after the guide wire 1 has been pulled out.

Figure 1D:
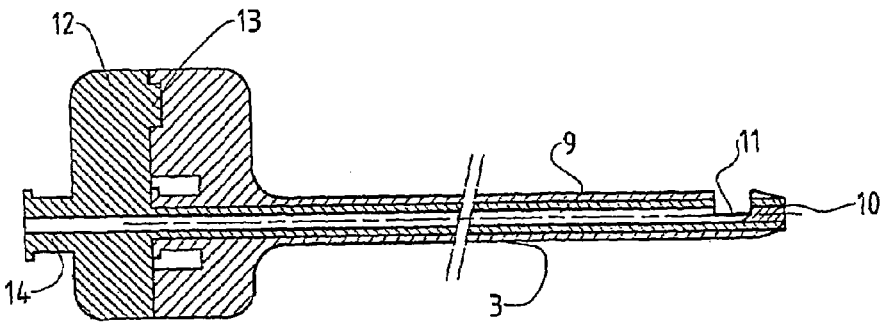

An inner cannula 9 is inserted in the cannula 3 in FIG. 1d. The outer diameter of this inner cannula is 3.0 mm, for instance, so that it can be pushed with play in the cannula 3. The inner diameter of the inner cannula can be 2.5 mm, for example. The front end 10 of the inner cannula is closed, and the length of the inner cannula 9 as well as the outer diameter of the end 10 are dimensioned such that, with completely inserted inner cannula 9, the orifice 4 of the cannula 3 is tightly sealed off. Located on the rear end of the inner cannula 9 is a handle 12, which is also of asymmetrical design, like the handle 6 of the cannula 3. The handle 12 has a protrusion 13, which forms together with the recess 7 provided on the handle 6 a snap in locking device. Furthermore the inner cannula 9 has a radial aperture 11 in the vicinity of the end 10, which radial aperture coincides with the aperture 5 of the cannula, with the snap in locking device 7, 13 in snapped-in state. The width of the radial aperture 11 of the inner cannula is somewhat less than its inner diameter, and the length of the aperture 11 is dimensioned in such a way that the exit cross-section of the aperture is at least just as large as the inner cross-section of the inner cannula 9. A coupling 14 provided on the handle 12 serves for attachment of a bone cement source, for instance a needle.

A bone cement injection with this first embodiment of the device according to the invention runs as follows. First, the guide wire 1 is driven in, as mentioned above. Then the cannula 3 is pushed over the guide wire 1 and pressed in until its radial aperture 5 sits at the place where the injection is supposed to take place. Now the guide wire 1 is pulled out and the inner cannula 9 is inserted in the cannula 3. After the two handles 6 and 12 are locked together by means of the snap in locking device and a needle with bone cement is connected with the coupling 14, the injection can begin. Thanks to the inventive design of the device, the physician is able to control the discharge direction of the bone cement into an area even during the injection by turning the two handles 6 and 12, locked together, and thus also the two radial apertures 5 and 11, aligned with one another.

Figure 2A:
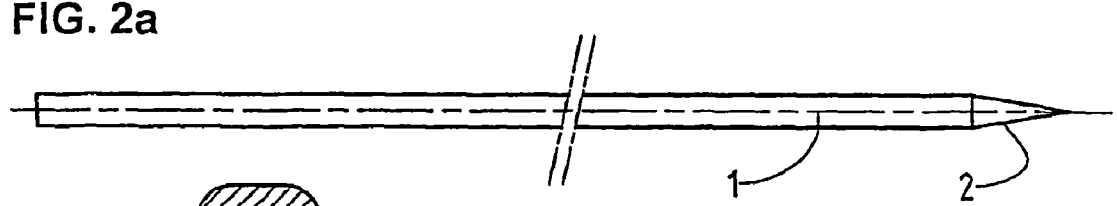
FIGS. 2a to 2f show a second embodiment example of a device according to the invention in which the cannula has a radial aperture and is closed in the front by a body.
Figure 2B:
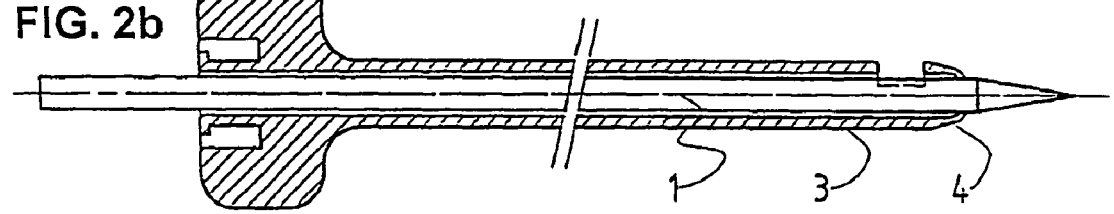
Figure 2C:
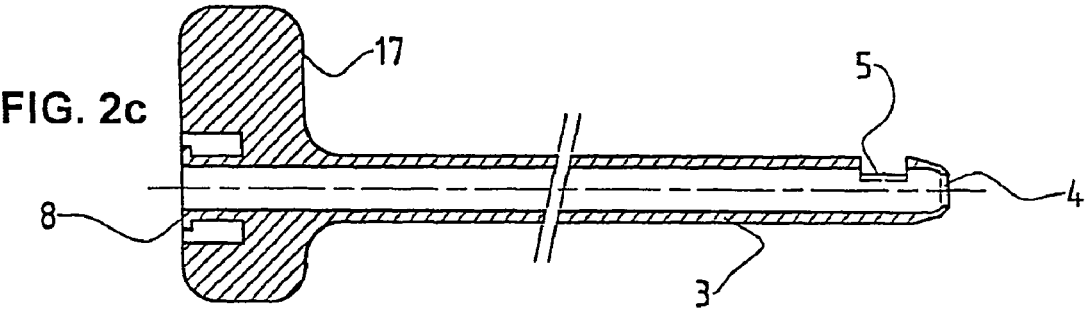
Figure 2D:
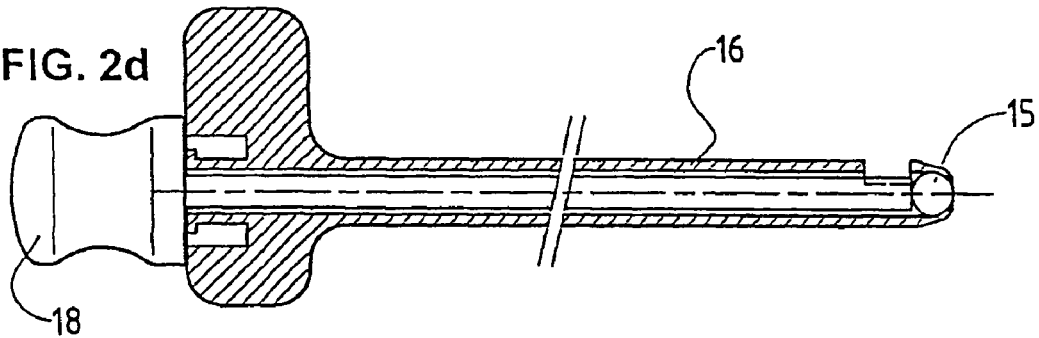
Figure 2E:
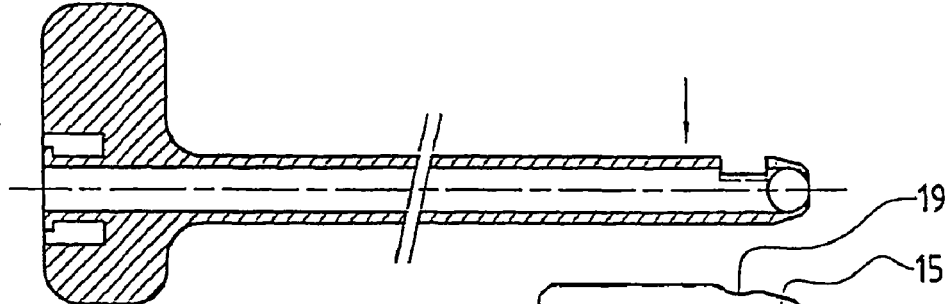
Figure 2F:

FIGS. 2a to 2f show a second embodiment of the device according to the invention, a guide wire 1 with a tip 2 being shown once again n FIG. 2a. The cannula 3 has in principle the same construction as that in the first embodiment example described above, which is why the same reference numerals have been used here. One difference is that with the cannula according to FIGS. 2b to 2e, the handle 17 is shaped differently from the handle 7 according to FIGS. 1b to 1d, and in particular has no recess 7 because in this second embodiment example there is no inner cannula 9. The orifice 4 of the cannula 3 is closed off with a ball 15 in this embodiment, which ball is pushed into its place with a plunger 16, as is shown in FIG. 2d, after pulling back of the guide wire 1. The plunger 16 has a support 18 and is so long that the ball 15 sits at the right place when the support 18 abuts the handle 17 of the cannula 3. In this embodiment example it is necessary for the orifice 4 of the cannula to be slightly reduced. The diameter of the ball 15 is slightly smaller than the inner diameter of the cannula 3, but somewhat larger than the inner diameter of the orifice 4 and also larger than the width of the radial aperture 5. In this way it is ensured that the ball 15 can be easily inserted into the cannula 3, but cannot escape through the radial aperture 5 or the orifice 4. So that the ball 15 does not roll back in an undesired way after it has been pushed in its place by the plunger 16, small indentations 19 are provided in the walling of the cannula 3, as is to be seen in FIG. 2f. The indentations are dimensioned in such a way that during pushing in of the ball 15 a certain resistance must be overcome.

This second embodiment type of the device according to the invention has the big advantage over the other embodiment types that no inner cannula is necessary and thus the entire inner cross-section of the cannula 3 is available for the flow of the bone cement. This results in a considerably lower pressure loss during injecting.

In the third embodiment example illustrated in FIGS. 3a to 3d a guide wire is likewise provided, as can be seen from FIG. 3a. The cannula here has the reference numeral 20, and differs from the previously described cannulae in that it has no radial aperture. Thus the handle 21 of the cannula 20 is also not asymmetrical. FIG. 3c shows an obturator 22 with which the physician makes space outside the orifice 24 of the cannula 20 after the insertion of the cannula 20 in order to then be able to insert the inner cannula 25, as is shown in FIG. 3d. The obturator 22 has a head 23 and its length is dimensioned such that when the head 23 abuts the handle 21 of the cannula, its front end projects so far out of the orifice 24 as the inner cannula 25 does later. The inner cannula 25 has a radial aperture 28, near its closed end 27, for exit of the bone cement. At the other end the inner cannula 25 has a handle 26 which is designed asymmetrically such that the situation of the radial aperture 28 can be seen from its position.

With this third embodiment of the invention a bone cement injection runs at the beginning the same way as with both other embodiments in that first the guide wire 1 is driven in and then the cannula 20 is pushed over the guide wire 1. After removal of the guide wire 1, the bone tissue is pushed back and compressed with the obturator 22 in the region of the orifice 24 so far that then the inner cannula 25 can be inserted without too much resistance. After insertion of the inner cannula 20<sic. 25>, its radial aperture is aligned as desired through turning of the handle 26, and the bone cement is injected with a needle connected by means of the coupling 14.

All three embodiments described of the device according to the invention thus allow an exact placement of the bone cement filling in that the discharge direction of the bone cement can be determined by turning the respective cannula and can even be changed during the injection.

So that both the cannula 3 according to the first embodiment example and the cannula 20 according to the third embodiment example can also be used for axial injection of bone cement, their handles 6 and 21 have a coupling 8 for direct attachment of a needle. The range of cannulae is thereby kept small.

What is claimed is:

1. Device for injecting bone cement, comprising a guide wire and a first cannula fitting on the guide wire at least with an inner diameter of a front axial orifice of the first cannula, and closing off means with which the front axial orifice of the first cannula is closable after removal of the guide wire, wherein the first cannula has a radial aperture, near the front axial orifice, for exit of the bone cement.

2. Device according to claim 1, wherein the closing off means is an inner cannula closed at a front end of the inner cannula, which inner cannula is insertable into the first cannula in such a way that the front end of the inner cannula tightly closes off the orifice of the first cannula and has a radial aperture near the front, closed end of the inner cannula.

3. Device according to claim 2, wherein a rear end of the first cannula has a first handle, a rear face of the first handle having a recess and a coupling, wherein a rear portion of the inner cannula has a handle having a protrusion which engages the recess of the handle of the first cannula.

4. Device according to claim 2, wherein a length of the radial aperture of the first cannula is at least the same as a length of the radial aperture of the inner cannula.

5. Device according to claim 2, wherein the radial aperture of the first cannula and the radial aperture of the inner cannula are alignable when the front end of the inner cannula tightly closes off the orifice of the first cannula and has the radial aperture near the front, closed end of the inner cannula.

6. Device according to claim 1, wherein the diameter of the front, axial orifice of the first cannula is smaller than the inner diameter of the first cannula and the closing off means is a stopper the largest diameter of which is greater than the diameter of the front, axial orifice of the first cannula.

7. Device according to claim 6, wherein the stopper has the shape of a ball.

8. Device according to claim 1, wherein the first cannula fits snugly on the guide wire at least with the inner diameter of the front axial orifice of the first cannula.

9. Device according to claim 1, wherein the first cannula fits sufficiently on the guide wire at least with the inner diameter of the front axial orifice of the first cannula to prevent substantial bone tissue from getting into the interior of the canula during forward pushing of the cannula along the guide wire into bone to a place where bone cement is supposed to be injected.

10. Device according to claim 1, wherein a rear end of the first cannula has a handle.

11. Device according to claim 1, wherein a rear end of the first cannula has an asymmetrical handle.

\* \* \* \* \*